United States Patent [19]

Kaplan

[11] 4,162,261

[45] Jul. 24, 1979

[54] NOVEL SOLVENTS FOR THE CATALYTIC PROCESS FOR MAKING POLYHYDRIC ALCOHOLS

[75] Inventor: Leonard Kaplan, Charleston, W. Va.

[73] Assignee: Union Carbide Corporation, New York, N.Y.

[21] Appl. No.: 832,384

[22] Filed: Sep. 13, 1977

Related U.S. Application Data

[63] Continuation-in-part of Ser. No. 727,646, Sep. 29, 1976, abandoned.

[51] Int. Cl.$^2$ ............................................. C07C 27/06
[52] U.S. Cl. ............................ 260/449 L; 260/449.5
[58] Field of Search ............. 260/449 R, 449 L, 449.5

[56] References Cited

U.S. PATENT DOCUMENTS

| 3,833,634 | 9/1974 | Pruett et al. | 260/449 R |
| 3,957,857 | 5/1976 | Pruett et al. | 260/449 R |

OTHER PUBLICATIONS

Christensen et al., Chem. Rev. (1964) vol. 74, No. 3, 351–359, 362, 368, 369, 371.

Primary Examiner—Howard T. Mars
Attorney, Agent, or Firm—Marylin Klosty

[57] ABSTRACT

This invention concerns making alkane polyols and monohydric alcohols by reacting hydrogen and oxides of carbon in the presence of a rhodium carbonyl complex dissolved in a crown ether.

9 Claims, 1 Drawing Figure

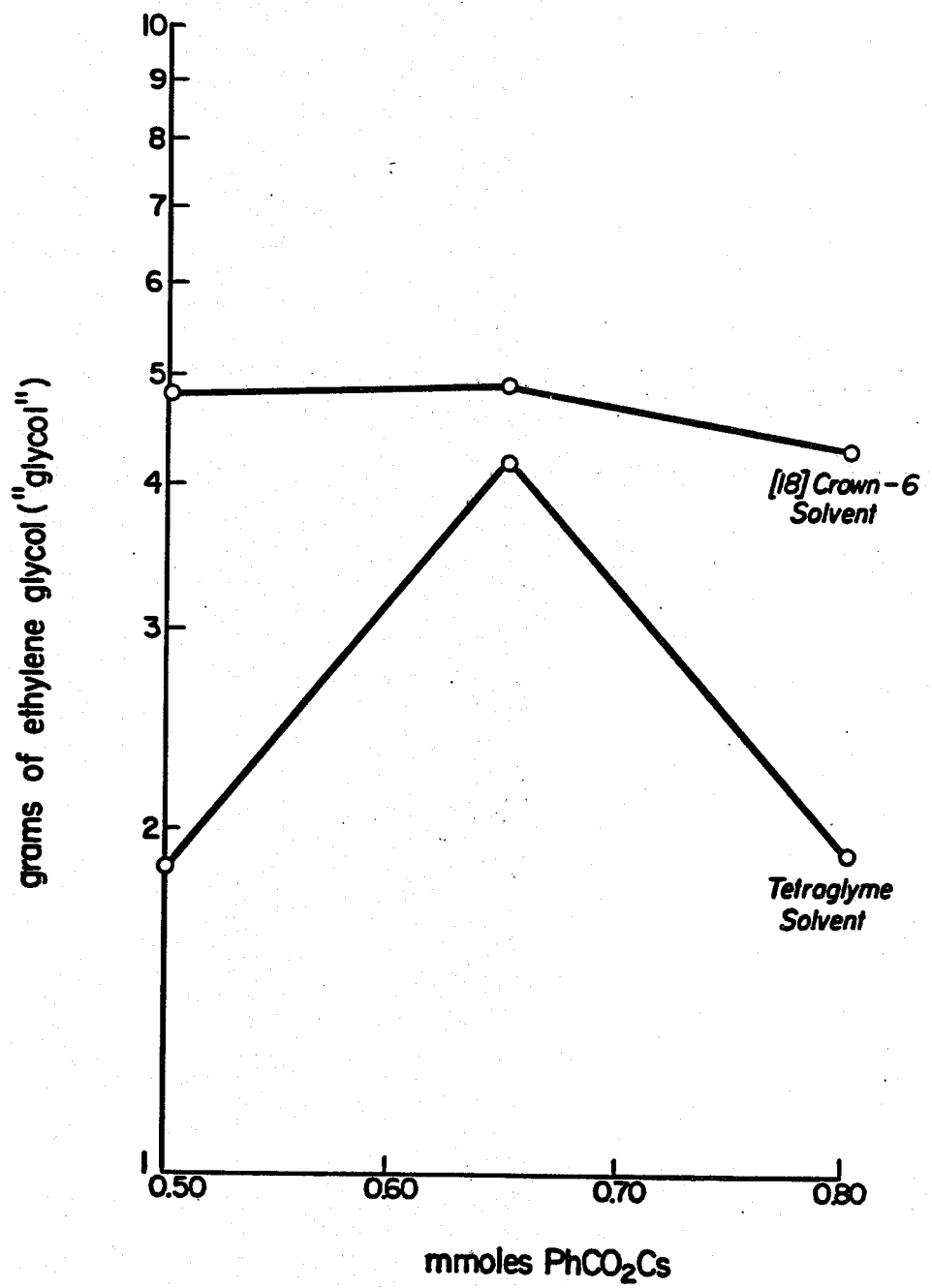

NOVEL SOLVENTS FOR THE CATALYTIC PROCESS FOR MAKING POLYHYDRIC ALCOHOLS

This application is a continuation-in-part of copending application Ser. No. 727,646, filed on Sept. 29, 1976, (now abandoned) both commonly assigned.

This invention is concerned with the manufacture of polyhydric alcohols, their ether and ester derivatives, and oligomers of such alcohols. This invention also produces monohydric alcohols such as methanol, and their ether and ester derivatives.

Polyhydric alcohols are presently being produced synthetically by the oxidation of petroleum derived materials. Owing to the limited availability of petroleum sources, the cost of these petroleum derived materials has been steadily increasing. Many have raised the dire prediction of a significant oil shortage in the future. The consequence of this has been the recognition of the need for a new low cost source of chemicals which can be converted into such polyhydric alcohols.

This invention is oriented to the process of making alkane diols and triols, containing 2, 3 or 4 carbon atoms, and derivatives such as their esters. Key products of the process of this invention are ethylene glycol and its ester derivatives. Byproducts of this invention are the lesser valuable, but valuable nevertheless, monohydric alkanols such as methanol, ethanol and propanols, and their ether and ester derivatives. The products of the process of this invention contain carbon, hydrogen and oxygen.

There are described in U.S. Pat. No. 3,833,634, issued Sept. 3, 1974, and U.S. Pat. No. 3,957,857, issued May 18, 1976, processes for reacting hydrogen and oxides of carbon in the presence of rhodium carbonyl complex catalysts. U.S. Pat. No. 3,957,857 is concerned with a rhodium carbonyl complex which is a rhodium carbonyl cluster exhibiting a particular infrared spectrum. The conditions, broadly speaking, employed in those processes involve reacting a mixture of an oxide of carbon and hydrogen with a catalytic amount of rhodium in complex combination with carbon monoxide, at a temperature of between about 100° C. to about 375° C. and a pressure of between about 500 p.s.i.a. to about 50,000 p.s.i.a. The patents discuss practicing the process in a homogeneous liquid phase mixture. This means that the rhodium catalyst is dissolved in an organic diluent, i.e., a solvent, liquid under the conditions of the reaction. In addition to the above U.S. Patents, the following U.S. Pat. Nos. and U.S. patent application Ser. Nos. amplify the development of the processes for making alkane polyols from mixtures of hydrogen and oxides of carbon:

U.S. Pat. No. 3,878,292, Patented Apr. 15, 1975;
U.S. Pat. No. 3,878,290, Patented Apr. 15, 1975;
U.S. Pat. No. 3,878,214, Patented Apr. 15, 1975;
U.S. Pat. No. 3,886,364, Patented May 27, 1975;
U.S. Pat. No. 3,940,432, Patented Feb. 24, 1976;
U.S. Pat. No. 3,929,969, Patented Dec. 30, 1975;
U.S. Pat. No. 3,952,039, Patented Apr. 20, 1976;
U.S. Pat. No. 3,948,965, Patented Apr. 6, 1976;
U.S. Pat. No. 3,944,588, Patented Mar. 16, 1976;
U.S. Pat. No. 3,974,259, Patented Aug. 10, 1976; (formerly U.S. Ser. No. 455,380, filed Mar. 27, 1974);
U.S. Ser. No. 455,379, Filed Mar. 27, 1974; (now U.S. Pat. No. 3,989,799, patented Nov. 2, 1976);
U.S. Ser. No. 526,942, Filed Nov. 25, 1974; (now U.S. Pat. No. 4,013,700, patented Mar. 22, 1977);
U.S. Ser. No. 488,139, Filed July 12, 1974; (now abandoned)
U.S. Pat. No. 3,968,136, Patented July 6, 1976; (formerly U.S. Ser. No. 488,140, filed July 12, 1974).
U.S. Ser. No. 506,862, Filed Sept. 17, 1974; (now abandoned)
U.S. Ser. No. 506,864, Filed Sept. 17, 1974; (now U.S. Pat. No. 4,001,289, patented Jan. 4, 1977);
U.S. Ser. No. 506,865, Filed Sept. 17, 1974; (now abandoned)
U.S. Ser. No. 511,750, Filed Oct. 3, 1974; (now abandoned);
U.S. Ser. No. 615,093, Filed Sept. 19, 1975;
U.S. Ser. No. 537,885, Filed Jan. 2, 1975; (now abandoned);
U.S. Ser. No. 618,023, Filed Sept. 30, 1975
U.S. Ser. No. 618,061, Filed Sept. 30, 1975, (now abandoned);
U.S. Ser. No. 618,021, Filed Sept. 30, 1975.

This invention constitutes an addition to or an improvement in the inventions of the foregoing patents and patent applications.

In the evolution of the processes characterized by U.S. Pat. Nos. 3,833,634 and 3,957,857, it was found that a desirable solvent in the homogeneous liquid phase system serves to separate ions without complexing the rhodium containing catalyst. In order to effect this result, the solvent should possess either a high dielectric constant or have the ability of complexing the available cations thereby freeing the available anions in the mixtures. For example, in U.S. Pat. Nos. 3,833,634 and 3,957,857, tetraglyme has been shown to be a particularly desirable solvent. It meets the above criteria because it is a good multidentate ligand for the available cations thereby reducing the interaction between the available cations and the available anions. On the other hand, as shown in U.S. application Ser. No. 615,093, sulfolane meets the above criteria because it possesses a high dielectric constant which decreases the force of attraction between oppositely charged ions in the mixture. Butyrolactone, as covered in Ser. No. 488,140, functions in the same manner as sulfolane as a solvent in the aforementioned processes. In U.S. application Ser. No. 618,021, there is disclosed the fact that when, e.g., sulfolane and tetraglyme are employed in these processes as a solvent mixture there are obtained higher productivity and greater retention of the rhodium catalyst in the homogeneous liquid phase mixture.

There are described herein new solvents for practicing the processes of the aforementioned U.S. Pat. Nos. and U.S. patent application Ser. Nos. for making alkane polyols. As a consequence of the use of these new solvents in these processes, the rate of formation of the alkane polyols such as ethylene glycol is greater than has been obtained from the use of any other solvent and/or solvent combination. In addition, these solvents provide the best retention of the rhodium catalyst in solution under the conditions which provide such higher rates of formation of alkane polyol.

The process of this invention involves as stated above the manufacture of alkane polyols. This includes the reaction of a mixture of hydrogen and oxides of carbon in a homogeneous liquid phase mixture containing a catalytic amount of rhodium carbonyl complex and the novel solvent. The reaction temperature is between about 100° C. and about 450° C. and at a pressure of between about 500 psia and 50,000 psia sufficient to produce the alkane polyol. The novel solvent is a cyclic organic compound which is liquid under the conditions of the reaction and can form a complex with a cation. The novel solvents of this invention are cyclic organic compounds known as crown ethers. They possess at least four (4) oxygen heteroatoms.

In the evolution of the processes of the aforementioned patents, certain significant evidence has been obtained which strongly supports the postulation that the rhodium carbonyl complex is in the form of an anion and consequently there must be cations present as well. This evidence includes direct observations and responses to variable and various factors in the operation of the processes. This includes: (1) infrared spectrums taken during the operation of the process, as well as periods prior and subsequent thereto and (2) response of rate and rhodium retention to nature and amount of promoters and solvent(s) employed. Involved in these classes of evidence are thousands of experiments the sum total of which state that by altering the mutual affinity of such anions and cations by choice of solvent, one can alter the rate of formation of alkane polyol and the retention of rhodium in the homogeneous liquid phase mixture. When one weakens the ion pairing of such anions and cations, the ability to produce more alkane polyol and retain more rhodium in the mixture is enhanced.

The solvent of this invention is selected for its known ability to complex with cations and the resulting structure of the complex. Involved in this selection is recognition of the kinds of cations present in the process which could interact with the available rhodium carbonyl complex anions. Armed with this foreknowledge, it is possible to select the solvent which provides the best capability of complexing that cation and produce a complex which has a low affinity for anions.

A simple experimental procedure for ascertaining the appropriate solvent of the class encompassed by this invention can be employed based upon the substantial information provided in the aforementioned patents and applications. A typical state of the art experiment for ascertaining the appropriate solvent is the following:

A 150 ml. capacity stainless steel reactor capable of withstanding pressures up to 7,000 atmospheres is charged with a premix of 75 cubic centimeters (cc) of solvent, 3.0 millimoles (mmol), 0.77 grams, of rhodium dicarbonylacetylacetonate, and the promoter(s). The reactor is sealed and charged with a gaseous mixture, containing equal molar amounts of carbon monoxide and hydrogen, to a pressure of 8,000 pounds per square inch (psig). Heat is applied to the reactor and its contents; when the temperature of the mixture inside the reactor reaches 190° C., as measured by a suitably placed thermocouple, an additional adjustment of carbon monoxide and hydrogen ($H_2$:$CO$ = 1:1 mole ratio) is made to bring the pressure back to 8000 psig. The temperature (in °C.) is raised to 240° C. and there maintained for 4 hours. During this period of time additional carbon monoxide and hydrogen is added whenever the pressure inside the reactor drops below about 7500 psig. With these added repressurizations the pressure inside the reactor is maintained at 8000 psig ±400 psig over the entire 4 hour period.

After the 4 hour period, the vessel and its contents are cooled to room temperature, the excess gas vented and the reaction product mixture is removed. Analysis of the reaction product mixture can be made by gas chromatographic analysis using a Hewlett Packard FM TM model 810 Research Chromatograph.

Rhodium recovery is determined by atomic absorption analysis of the contents of the reactor after the venting of the unreacted gases at the end of the reaction. A further analysis may be run on a "wash" of the reactor. The wash of the reactor consists of charging to the reactor 100 cc of the solvent used for that experiment, and bringing the reactor and its contents to a temperature of 160° C. and a pressure of 14,000 to 15,000 psig and maintaining these conditions for a period of 30 minutes. The reactor is then cooled and the unreacted gases vented and an atomic absorption analysis for rhodium is run on the reactor's contents.

The above procedure can be repeatedly run with the solvent of choice with different amounts of the promoter and from the rates of ethylene glycol formation and the amounts of rhodium retained in solution, the solvent can be rated vis-a-vis other solvents commonly employed in this art. Though the above procedure is carried out a 240° C., one may make the comparison at a higher temperature (e.g., 260° C.) and thereby make the rating of the solvent of choice based on a more critical standard. Illustrative of a comparison of this kind, reference is made to the drawing which graphically depicts the use of cesium benzoate as the promoter in the above experimental procedure (in this case run at 220° C.) with tetraglyme or [18]-crown-6 as the solvents. As the graph shows, increase in the promoter content in the tetraglyme solvent runs results in a dramatic decrease in the amount of ethylene glycol produced when the promoter content exceeds that amount which achieves the maximum amount in that system. In the case of [18]-crown-6, a highly preferred solvent of this invention, this degree of drop-off in rate of production does not occur and the maximum of ethylene glycol produced is greater also.

The class of compounds which are employed as solvents in this invention are described in considerable detail in a host of publications, the more significant of which survey and characterize by illustration and references the depth of knowledge existing on these compounds:

(1) "Structure and Bonding," vol. 16, 1973, published by Springer-Verlag, New York, N.Y., excluding the article by Simon et al, pp. 113–160, and, in particular, emphasis should be given to the article by J. Lehn, pp. 1–69, and the definitions of types of complexes at p. 13, under which can be found the above definition for the aforementioned class of preferred solvents.

(2) J. Lipkowski, *Wiadomosci Chemiczne*, 29, pp. 435–450 (1975).

(3) Cram et al., *Pure and Applied Chemistry*, vol. 43, pp. 327–349 (1975).

(4) Gokel et al., *Aldrichimica Acta*, vol. 9, pp. 3–12 (1976).

(5) Christensen et al., *Chemical Reviews*, vol. 74, No. 3, pp. 351–384 (1974); note at page 351 the general characterization of the organic macrocycles employable herein as solvent, in particular, the definition of the "novel macrocycles" which is hereinafter adopted in modified form as a mode of describing this class of preferred solvents ... "macrocycles typically contain central hydrophilic cavities ringed with ... electronegative ... binding atoms and exterior ... frameworks exhibiting hydrophobic behavior. They show a pronounced ability to bind a wide variety of cation . . . and in many cases to undergo . . . conformational changes during binding."

Included in these publications are representative illustrations of crown ethers as above described and limited which can be employed as solvents herein and it is believed that in no instance do these publications and the references contained in each recite a crown ether which is so limited that it cannot be employed in the practice of this invention. However, one should not confuse the crown ethers and the crown ethers complexed with cations as depicted in this literature because this invention is concerned with the use as solvents of the crown ethers and not such complexes other than those in situ produced in the practice of this invention.

For an ample description of crown ethers, their structures and nomenclature, reference is made to Pedersen, J.A.C.S., Vol. 89, No. 29, pp. 7017–7036 (Dec. 20, 1967), and ADI Document No. 9583 (see footnote (11) on p. 7017 of J.A.C.S. article), which is certified by the Library of Congress on Aug. 16, 1976, as being "available to the general public Aug. 14, 1967," which is based on Pedersen, *Communications to The Editor*, J.A.C.S., Vol. 89, No. 10, pp. 2495–2496 (May 10, 1967). In addition, further publications of such crown ethers are U.S. Pat. No. 3,562,295, to Pedersen, issued Feb. 9, 1971, on an application filed Dec. 18, 1968, U.S. Pat. No. 3,965,116, to Cram, issued June 22, 1976, on an application filed Sept. 12, 1974, U.S. Pat. No. 3,966,766, to Lehn, issued June 29, 1976, U.S. Pat. No. 3,860,611, to Krespan, issued Jan. 14, 1975, and U.S. Pat. No. 3,952,015, to Krespan, issued Apr. 20, 1976. All of the Crown ethers described in those publications cited above, especially in the Pedersen publications, notes (1) "Structure and Bonding" and (5) Christensen et al., to the extent that they meet the structural limitations recited herein for the solvents of this invention, may be used in the practice of this invention.

The crown ethers of this invetnion contain in the principle ring at least 4 oxygen atoms each separated from the other by at least two aliphatic carbon atoms in series. In the preferred embodiment, the principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or mixtures of them. The maximum number of ring oxygen atoms in the principal ring may be as much as about 100, however, it is desirable that those ring oxygen atoms joined to groups other than ethylene or substituted ethylene number not more than about 50 when the number of such ring oxygen atoms exceeds about 52.

The crown ethers of this invention consist essentially of carbon, hydrogen and oxygen. Minor amounts of other atoms which do not appreciably contribute to the solvency function of the crown ether according to this invention may be used. The crown ether may be termed monocyclic or polyclic, such as the following types of crown ether structures schematically characterized without reference to numbers and kinds of atoms:

Monocyclic    Bicyclic    Tricyclic
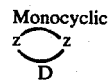
D

-continued
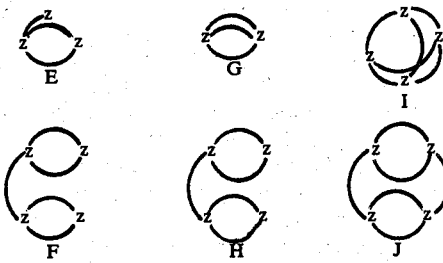

(See Note (1) "Structure and Bonding," article by Lehn, supra, p. 11)

The methods by which such crown ethers can be produced has been established, see Note (1) "Structure and Bonding," article by Lehn, supra, pp 25–36.

Because of the ease of manufacture of the monocyclic crown ethers in commercial quantities, they are the preferred crown ethers in the practice of this invention. One synthetic method to make the crown ethers employs the Williamson synthesis* and can be carried by one of the following paths:

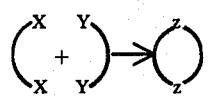 ("a)

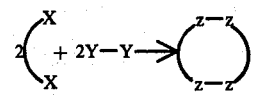 (b)

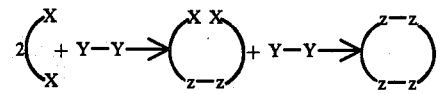 (c)

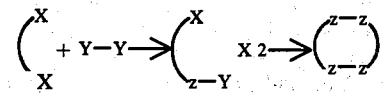 (d)

"Three procedures, (a), (c) and (d), involve condensations of only two partners, whereas in the case of (b) four reactive molecules are condensed in one synthetic step." (See Lehn article, supra, note (1) above.)

*See Feiser & Fieser, Organic Chemistry, 3rd ed., 1956, p. 136. Halides can be replaced by any ester such as acylates, sulfonates and sulfates.

The crown ethers may be made by the known Lewis acid catalyzed polymerization of alkylene oxides, such as ethylene oxide, and 1,2-propylene oxide.

This invention does not reside in the manufacture and composition of crown ethers only in their use as a solvent according to this description.

As a general rule, the advantages of said crown ethers as a solvent over other known solvents used in making alkane polyols from synthesis gas decrease as the number of carbons in the crown ether increases in relation to a fixed number of ether oxygen. However, the crown ethers covered by this invention, regardless of the carbon to ether oxygen ratio, will always function as a suitable solvent for effecting the reaction to produce some alkane polyol. Therefore, in optimizing the benefits of this invention, said crown ethers which have the lowest amount of carbon to ether oxygen ratio are preferred. In the most preferred embodiment, the crown ether solvent contains 4 to 15 ether oxygens in the principal ring thereof.

The substituted ethylene, trimethylene and tetramethylene contain as substituents such groups as alkyl of 1 to about 8 carbon atoms; cycloalkyl of from about 4 to about 8 carbon atoms; hydroxyl bonded to non-ether oxygen bonded carbon atoms; hydroxyalkyl of 1 to about 8 carbon atoms; hydroxyalkyloxyalkylene; oxyalkylene of from 2 to about 4 carbon atoms; carboxylates bonded to the ring of the crown ether either through a ring carbon, an alkyl group or an oxyalkyl unit; acyl; oxycarbonyl bonded to non-ether oxygen bonded carbon atoms; and alkylene which form a fused or spiro ring with ring forming carbon atoms; and the like.

Illustrative of such substituents are alkyl groups such as methyl, ethyl, n-propyl, n-butyl, isobutyl, n-amyl, isoamyl, n-hexyl, 2-ethylhexyl, n-octyl; cycloalkyl groups such as cyclobutyl, cyclopentyl, cyclohexyl, cyclooctyl; hydroxyalkyl groups such as hydroxymethyl, 2-hydroxyethyl, 2-hydroxypropyl, 3-hydroxypropyl, 2-hydroxybutyl, 4-hydroxybutyl, 4-hydroxybutyl, 6-hydroxyhexyl; hydroxyalkyloxyalkylene where the hydroxyalkyl is as described above and the oxyalkylene is as described immediately below; oxyalkylene which is a group of the formula:

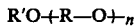

wherein the free valence is bonded to alkyl of 1 to 4 carbon atoms or non-ether oxygen bonded ring carbon atoms, R is alkylene of 2 to 4 carbon atoms, R' is hydrogen or alkyl of 1 to about 4 carbon atoms and n is 1 to about 113, preferably 1 to about 50; acyl of the formula:

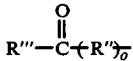

wherein R" is alkylene of 1 to about 8 carbon atoms, R''' is alkyl of 1 to about 4 or alkylene bonded to R" to form a closed ring containing 4 to about 8 carbon atoms, and o is 0 or 1; carboxylates and oxycarbonyl of the formula:

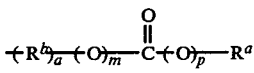

wherein a, m and p may have a value of 0 or 1, provided that when m is 1, a can be 0 provided the substituent is bonded to a non-ether oxygen bonded carbon, and when m or p is 1 and the other is zero; $R^a$ is alkyl of 1 to about 12 carbon atoms or oxyalkylene as described above, and $R^b$ is alkyl of 1 to about 12 carbon or oxyalkylene, as described above; and/or an alkylene radical which form a fuse or spiro ring with ring forming carbon atoms, such as:

wherein $R^c$ is alkylene of from 3 to about 7 carbon atoms or oxyalkylene, as described above; $R^d$ is alkylene containing 1 or 2 carbon atoms, and any free valences of $R^d$ not bonded to $R^c$ or ring forming carbon atoms of the crown ether are bonded to hydrogen.

The solvents of this invention may be employed as the sole solvent in carrying the process of this invention or they may be mixed with other known solvents as set forth in the aforementioned patents and patent applications relating to the manufacture of alkane polyols from the reaction of hydrogen and, e.g., CO in the presence of a rhodium carbonyl complex catalyst. It should be appreciated that this invention contemplates the use of the solvents of this invention with other materials which heretofore have not been employed as a solvent in those patents and patent applications. Mixtures of the novel solvents herein defined and disclosed are contemplated. The amount of the novel solvents of this invention should comprise at least ten (10) weight percent of the reaction solution, i.e., the homogeneous liquid phase mixture exclusive of products formed in the mixture in carrying out the process.

In order to obtain a beneficial effect from use of a solvent mixture, as compared to either pure component, the component's modes of action should be different. Use of a mixture could yield results which need not be intermediate of those obtained from use of either solvent because they could act synergistically, not merely complimentarily, and the degree of harmful ion pairing could be less than in either solvent. [18]-crown-6 is a good solvent at least in part because of its complexing ability. Therefore, its best co-solvents should have high dielectric constants.

The novel solvents of this invention can be combined with gamma-butyrolactone, sulfolane and/or tetraglyme much as sulfolane and tetraglyme are employed together as described in Ser. No. 618,021, filed Sept. 30, 1975.

The ratio of these novel solvents to tetraglyme and/or sulfolane or gamma-butyrolactone, preferably sulfolane and gamma-butyrolactone, that one employs in the solvent mixture providing the homogeneous liquid phase reaction mixture is predicated upon the conditions of the reaction. As a guideline, it is desired that such solvent ratio be selected to provide a rate of formation of the alkane polyol which is greater than would be obtained under the same conditions of reaction in either tetraglyme or sulfolane, or a mixture of both, or in either gamma-butyrolactone, or mixtures of tetraglyme with butyrolactone.

This ratio of the novel solvents to sulfolane on/or gamma-butyrolactone or tetraglyme alone or with gamma-butyrolactone or sulfolane, hereinafter referred to as the "solvent ratio," may range from 1 to 10 to 50 to 1, determined on a volume basis. However, it is to be emphasized that in any reaction system, such factors as the ratio of carbon monoxide to hydrogen, temperature and pressure selected, concentrations of added components such as catalysts and promoters, the nature of the promoter, play a role in determining what solvent ratio is most effective. In one system the volume ratio of the novel solvent to tetraglyme and/or sulfolane or gamma-butyrolactone with or without tetraglyme may be optimum at a value of 1 whereas in another the optimum solvent ratio is 2. This statement is made to emphasize the point that when selecting the appropriate solvent ratio one will be required to explore in a number of experiments in a given reaction system a number of ratios such that the optimum solvent ratios can be determined.

The term sulfolane as used herein and in the claims is intended to cover tetramethylene sulfone and substituted tetramethylene sulfone which provide essentially the same advantages as a result of their solvent characteristics as tetramethylene sulfone. Illustrative of substituted sulfolanes which are of a kind that may be suitable as a cosolvent with the novel solvents in the practice of this invention are those which are characterized by the following formula:

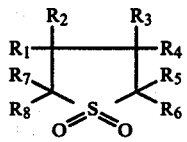

wherein each of $R_1$ through $R_8$ is at least one of hydrogen; hydroxyl; straight or branched chain alkyl, preferably having from 1 to 12 carbon atoms, most preferably 1 to 6 carbon atoms in the alkyl chain, such as methyl, ethyl, isopropyl, butyl, octyl, dodecyl and the like; a cycloaliphatic group including the monocyclic and bicyclic groups such as cyclopentyl, cyclohexyl, bicyclo [2.2.1] heptyl, and the like; or an aryl, alkyl-aryl, or aralkyl group such as phenyl, naphthyl, xylyl, tolyl, benzyl, beta-phenylethyl and the like; an ether of the formula —(O—R°) wherein R° may be aryl or lower alkyl having from 1 to 12 carbon atoms, preferably 1 to 4 carbon atoms in the alkyl chain; an alkylene or polyalkylene ether of the formula —$(OC_nH_{2n})_x$—OR°° wherein n has an average value of from 1 to about 4, x has an average value of from 1 to about 150, preferably 1 to about 20, most preferably 1 to about 4, and R°° may be hydrogen or alkyl having from 1 to 6 carbon atoms in the alkyl chain, such as poly(oxyethylene), poly(oxypropylene), poly(oxyethylene-oxypropylene), alkylene and polyalkylene glycols and lower alkyl ethers thereof; a carboxylate group of the formula:

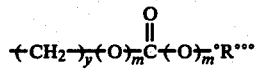

wherein y may have any value between 0 and 12, m and m° may be zero or one provided that when either m or m° is one the other is zero, and R°°° may be a lower alkyl group having from 1 to 12 carbon atoms, preferably from 1 to 4 carbon atoms, or aryl; provided that not all of the $R_{1-8}$'s are hydrogen.

Preferably the sulfolane used in the practice of the present invention is tetramethylene sulfone, i.e., tetrahydrothiophene-1,1-dioxide. In those instances where it may be desirable to use a substituted sulfolane those substituted in the 3 or 3,4 positions of the sulfolane ring are preferred.

The rhodium carbonyl complexes suitable for use in the practice of the present invention are those wherein the complex is at least one of (1) rhodium in complex combination with carbon monoxide, (2) rhodium in complex combination with carbon monoxide and hydrogen, (3) rhodium in complex combination with carbon monoxide and at least one Lewis base, (4) rhodium in complex combination with carbon monoxide, hydrogen and at least one Lewis base, and (5) mixtures thereof.

Moreover, the rhodium carbonyl complexes of this invention may be in the form of rhodium carbonyl clusters. P. Chini, in a review article entitled "The Closed Metal Carbonyl Clusters" published in Review (1968). Inorganica Chimica Acta, pages 30–50, states that a metal cluster compound is "a finite group of metal atoms which are held together entirely, mainly, or at least to a significant extent, by bonds directly between the metal atoms even though some non-metal atoms may be associated intimately with the cluster." The rhodium carbonyl cluster compounds of this invention contain rhodium bonded to rhodium or rhodium bonded to another metal, such as cobalt, and/or iridium. The preferred rhodium carbonyl cluster compounds of this invention are those which contain rhodium-rhodium bonds. These compounds desirably contain carbon and oxygen in the form of carbonyl (—C—O), in which the carbonyl may be "terminal," "edge-bridging", and/or "face-bridging." They may also contain hydrogen and carbon in forms other than carbonyl. The following are illustrative of what is believed to be the structure of two distinct rhodium carbonyl clusters and both are suitable for use in this invention.

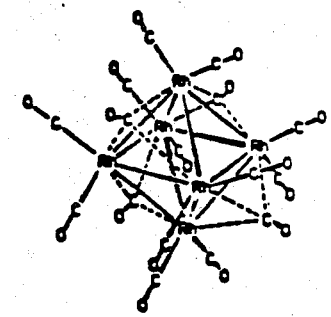

$Rh_6(CO)_{16}$

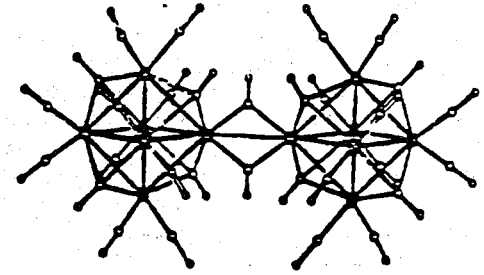

$[Rh_{12}(CO)_{30}]^{2-}$

The structures of the rhodium carbonyl clusters may be ascertained by X-ray crystal diffraction, nuclear magnetic resonance (NMR) spectra, or infrared spectra as disclosed in the article entitled "Synthesis and Properties of the Derivatives of the $[Rh_{12}(CO)_{30}]^{2-}$ Anion" by P. Chini and S. Martinengo; appearing in Inorganica Chinica Acta, 3:2 pp 299–302, June (1969). Of particular analytical utility in the present invention is the use of infrared spectroscopy which allows for characterization of the particular rhodium carbonyl complex present during the operation of the process of the present invention.

The rhodium carbonyl complex is, as characterized above, a rhodium containing compound in which the rhodium is complexed with CO. This can be achieved with just carbon monoxide or in addition to the carbon monoxide there may be included hydrogen and/or organic or inorganic Lewis base promoters to create the complex. In the last case, "complex" means a coordination compound formed by the union of one or more electronically rich molecules or atoms capable of independent existence with one or more electronically poor molecules or atoms, each of which is also capable of independent existence. The precise role of these Lewis bases in the reaction of the present invention is not fully appreciated at present. They may be functioning as ligands and/or forming counter-ions under the reaction conditions of the present process or they may be functioning just merely as Lewis bases and neutralizing or tying up a molecular species which if allowed to remain "free" or in its non-base-bound state would adversely affect the productivity of the present invention.

Organic Lewis bases which are suitable in the practice of the present invention contain at least one Lewis base oxygen atom and/or one Lewis base nitrogen atom said atoms possessing a pair of electrons available for the formation of coordinate bonds. In suitable embodiments the organic Lewis bases contain from 1 and upwards to 4 Lewis base atoms, preferably from 1 to 3 such atoms, and most preferably 1 or 2 Lewis base atoms. These organic Lewis bases are said to be multidentate or polydentate, that is to say, they are bidentate, tridentate, or quadridentate, depending on whether 2, 3 or 4 Lewis base atoms are involved.

Those organic Lewis bases which contain at least one Lewis base nitrogen atom plus at least one Lewis base oxygen atom will oftentimes hereinafter be referred to as "organic aza-oxa" Lewis bases.

Suitable organic nitrogen Lewis bases ("aza" only) most generally contain carbon, hydrogen, and nitrogen atoms. Suitable organic oxygen Lewis bases most generally contain carbon, hydrogen, and oxygen atoms. Suitable organic aza-oxa Lewis bases most generally contain carbon, hydrogen, oxygen, and nitrogen atoms. The carbon atoms can be acyclic and/or cyclic such as aliphatic, cycloaliphatic, aromatic (including fused and bridged) carbon atoms, and the like. Preferably, the organic Lewis bases contain from 2 to 60, most preferably 2 to 40 carbon atoms. The nitrogen atoms can be in the form of imino (—N=), amino (—N—), nitrilo (N≡), etc. Desirably, the Lewis base nitrogen atoms are in the form of imino nitrogen and/or amino nitrogen. The oxygen atoms can be in the form of groups such as hydroxyl (aliphatic or phenolic), carboxyl

carbonyloxy

oxy (—O—), carbonyl

etc., all of said groups containing Lewis base oxygen atoms. In this respect, it is the "hydroxyl" oxygen in the

group and the "oxy" oxygen in the

group that are acting as the Lewis base atoms. The organic Lewis bases may also contain other atoms and/or groups such as alkyl, cycloalkyl, aryl, chloro, trialkylsilyl, and the like.

Illustrative organic oxygen Lewis bases include, by way of illustrations, glycolic acid, methoxyacetic acid, ethoxyacetic acid, diglycolic acid, diethyl ether, tetrahydrofuran, dioxane, tetrahydropyran, pyrocatechol, citric acid, 2-methoxyethanol, 2-ethoxyethanol, 2-n-propoxyethanol, 2-n-butylethanol, 1,2,3-trihydroxybenzene, 1,2,4-trihydroxybenzene, 2,3-dihydroxynaphthalene, cyclohexane-1,2-diol, oxetane, 1,2-dimethoxybenzene, 1,2-diethoxybenzene, methyl acetate, ethanol, 1,2-dimethoxyethane, 1,2-diethoxyethane, 1,2-di-n-propoxyethane, 1,2-di-n-butoxyethane, pentane-2,4-dione, hexane-2,4-dione, heptane-3,5-dione, octane-2,4-dione, 1-phenylbutane-1,3-dione, 3-methylpentane-2,4-dione; the mono- and dialkyl ethers of propylene glycol, of diethylene glycol, of dipropylene glycol; and the like.

Illustrative organic aza-oxa Lewis bases include, for example, the alkanolamines, such as, ethanolamine, diethanolamine, isopropanolamine, di-n-propanolamine, and the like; N,N-dimethylglycine, N,N-diethylglycine; iminodiacetic acid, N-methyliminodiacetic acid; N-methyldiethanolamine; 2-hydroxypyridine, 2,4-dihydroxypyridine, 2-methoxypyridine,, 2,6-dimethoxypyridine, 2-ethoxypyridine; lower alkyl substituted hydroxypyridines, such as 4-methyl-2-hydroxypyridine, 4-methyl-2,6-dihydroxypyridine, and the like; morpholine, substituted morpholines, such as 4-methylmorpholine, 4-phenylmorpholine; picolinic acid, methyl-substituted picolinic acid; nitrilotriacetic acid, 2,5-dicarboxypiperazine, N-(2-hydroxyethyl) iminodiacetic acid, ethylenediaminetetraacetic acid; 2,6-dicarboxypyridine; 8-hydroxyquinoline, 2-carboxyquinoline, cyclohexane-1,2-diamine-N,N,N',N'-tetraacetic acid, the tetramethyl ester of ethylenediamine-tetraacetic acid, and the like.

Illustrative of the Lewis base nitrogen ("aza") containing compounds suitable for use in the practice of the present invention are ammonia and the amines. Any primary, secondary, or tertiary amine is suitable in the practice of the present invention. This includes the mono-, di-, tri-, and polyamines and those compounds in which the Lewis base nitrogen forms part of a ring structure as in pyridine, quinoline, pyrimidine, morpholine, hexamethylenetetraamine, and the like. In addition any compound capable of yielding an amino nitrogen under the reaction conditions of the present invention is suitable, as in the case of an amide, such as formamide and urea, or an oxime. Further illustrative of these Lewis base nitrogen compounds are ammonia; aliphatic amines such as methylamine, ethylamine, n-propylamine, isopropylamine, octylamine, dodecylamine, dimethylamine, diethylamine, diisoamylamine, methylethylamine, diisobutylamine, trimethylamine, methyldiethylamine, triisobutylamine, tridecylamine, and the like; aliphatic and aromatic di- and polyamines such as 1,2- ethanediamine, 1,3-propanediamine, N,N,N',N'-tetramethylenediamine, N,N,N',N'-tetraethylethylenediamine, N,N,N',N'-tetra-n-propylethylenediamine, N,N,N',N'-tetrabutylethylenediamine, o-phenylenediamine, m-phenylenediamine, p-phenylenediamine, p-tolylenediamine, o-tolidene, N,N,N',N'-tetramethyl-p-phenylenediamine, N,N,N',N'-tetraethyl-4,4'-biphenyldiamine, and the like; aromatic amines such as aniline, 1-naphthylamine, 2-naphthylamine, p-toluidine, o-3-xylidine, p-2-xylidine, benzylamine, diphenylamine, dimethylaniline, diethylaniline, N-phenyl-1-naphthylamine, bis-(1,8)-dimethylaminonaphthalene, and the like; alicyclic amines such as cyclohexylamine, dicyclohexylamine, and the like; heterocyclic amines such as piperidine; substituted piperidines such as 2-methylpiperidine, 3-methylpiperidine, 4-ethylpiperidine, and 3-phenylpiperidine; pyridine; substituted pyridines such as 2-methylpyridine, 2-phenylpyridine, 2-methyl-4-ethylpyridine, 2,4,6-trimethylpyridine, 2-dodecylpyridine, 2-chloropyridine, and 2-(dimethylamino)pyridine; quinoline; substituted quinolines, such as 2-(dimethylamino)-6-methoxyquinoline; 4,5-phenanthroline; 1,8-phenanthroline; 1,5-phenanthroline; piperazine; substituted piperazines such as N-methylpiperazine, N-ethylpiperazine, 2,N-dimethylpiperazine; 2,2'-dipyridyl; methyl-substituted 2,2'-dipyridyl; ethyl-substituted 2,2'-dipyridyl; 4-triethylsilyl-2,2'-dipyridyl; 1,4-diazabicyclo[2.2.2]octane, methyl substituted 1,4-diazabicyclo[2.2.2]octane, purine and the like.

Illustrative of the inorganic Lewis bases useful in the practice of the present invention are ammonia, hydroxides and halides, such as chloride, bromide, iodide, or fluoride; or mixtures thereof.

Any of the above Lewis bases may be provided to the reaction in compound form or as ligands which are in complex combination with the rhodium carbonyl compound initially charged to the reactor.

The precise role of the rhodium carbonyl complexes, such as the rhodium carbonyl clusters characterized previously, in the reaction of hydrogen with oxides of carbon to produce polyhydric alcohols is not fully appreciated at present. Under the reaction conditions of the present process the carbonyl complexes are believed to be anionic in their active forms. Rhodium carbonyl anions are known to be involved in the following set of reactions as indicated by S. Martinengo and P. Chini, in Gazz. Chim. Ital., 102, 344 (1972) and the references cited therein.

carbon monoxide and hydrogen to the polyhydric alcohol.

Assuming the active catalytic species is a rhodium carbonyl complex anion, or the formation of the active species under reaction conditions is directly dependent on the existence of these anions, allows one to better explain, in terms of reaction rates, productivity and catalyst stability, the role the solvents play in the reaction whereby hydrogen and an oxide of carbon are converted to the polyhydric alcohol. It is believed that the solvents enhance the reactivity of these rhodium carbonyl complex anions because a "naked," reactive anion is produced. Naked rhodium carbonyl anions are believed to be produced under the reaction conditions of the present process because the solvent decreases any tendency of the rhodium carbonyl anions to ion pair, the rhodium carbonyl anions are not strongly solvated, nor is the rhodium strongly complexed by the solvent all of which tend to produce an anion having a higher degree of reactivity under the reaction conditions employed.

The novel process is suitably effected over a wide superatmospheric pressure range of from about 800 psia to about 50,000 psia. Pressures as high as 50,000 psia, and higher can be employed but with no apparent advantages attendant thereto which offset the unattractive plant investment outlay required for such high pressure equipment.

In one embodiment of this invention the upper pressure limitation is approximately 16,000 psia. Effecting the present process below about 16,000 psia, especially below about 13,000 psia, and preferably at pressures below about 8000 psia, results in cost advantages which are associated with low pressure equipment requirements. However, when practicing the present invention at pressures below about 12,000 psia, the rate of desired product formation is quite slow and in order to obtain a faster reaction rate and/or higher conversions to the desired product there is provided to the reaction a promoter which may be a salt and/or an organic Lewis base nitrogen compound. In those instances where the Lewis base nitrogen compound is contained as a ligand in the rhodium carbonyl complex charged to the reactor or where anion of the salt promoter charged to the reactor is a rhodium carbonyl complex such as cesium triacontacarbonylrhodate, it may not be necessary to add to the reaction any additional amounts of these promoters. A suitable pressure range for effecting the

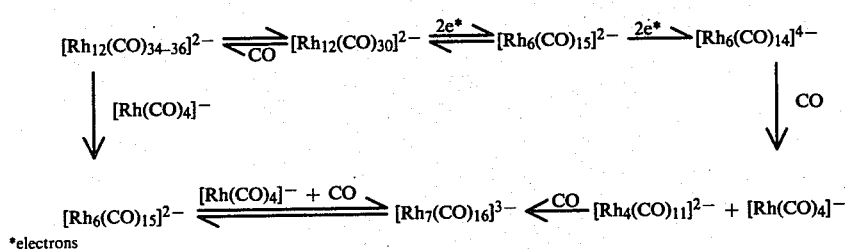

(I)

*electrons

Infrared spectra under reaction conditions of the present process have shown both the $Rh(CO)_4^-$ and $[Rh_{12}(CO)_{34-36}]^{2-}$ anions to be present at various concentrations at different times of the reaction. Therefore the set of reactions and equilibria shown in I above may represent the active rhodium carbonyl species responsible for polyhydric alcohol formation or may be merely symptomatic of some further intermediate transitory rhodium carbonyl structure which serves to convert the reaction in the presence of these promoters is from about 1000 psia to about 16,000 psia, preferably from about 4000 to about 16,000 psia.

In a preferred embodiment of the present invention the pressures referred to above represent the total pressures of hydrogen and oxides of carbon in the reactor.

Suitable salts useful in the practice of the present invention at pressures below about 16,000 psia include any organic or inorganic salt which does not adversely affect the production of polyhydric alcohols. Experimental work completed to date indicates that any salt will show this promoter effect under some, but not all, glycol-producing conditions. Illustrative of the salts useful in the practice of the present invention are the ammonium salts and the salts of the metals of Group I and Group II of the Periodic Table (Handbook of Chemistry and Physics—50th Edition) for instance the halide, hydroxide, alkoxide, phenoxide and carboxylate salts such as sodium fluoride, potassium acetate, cesium floride, cesium pyridinolate, cesium formate, cesium acetate, cesium benzoate, cesium p-methylsulfonyl benzoate ($CH_3SO_2C_6H_4COO$)Cs, rubidium acetate, magnesium acetate, strontium acetate, ammonium formate, ammonium benzoate and the like.

Also useful in the practice of the present invention are organic salts of the following formula:

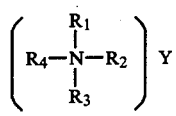

quaternary ammonium salts

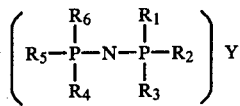

bis (triorgano phosphine)iminium salts wherein $R_1$ through $R_6$ in formulas (II) and (III) above are any organic radicals which do not adversely affect the production of polyhydric alcohols by reacting oxides of carbon with hydrogen in the presence of the aforedefined rhodium carbonyl complex, such as a straight or branched chain alkyl group, having from 1 to 20 carbon atoms in the alkyl chain, such as methyl, ethyl, n-propyl, isopropyl, n-butyl, octyl, 2-ethylhexyl, dodecyl, and the like; or a cycloaliphatic group including the monocyclic and bicyclic groups cyclopentyl, cyclohexyl, and bicyclo[2.2.1]heptyl groups, and the like or an aryl, alkylaryl, or aralkyl group such as phenyl, naphthyl, xylyl, tolyl, t-butylphenyl, benzyl, beta-phenylethyl, 3-phenylpropyl and the like; for a functionally substituted alkyl such as beta-hydroxyethyl, ethoxymethyl, ethoxyethyl, phenoxyethyl, and the like; or a polyalkylene ether group of the formula $-(C_nH_{2n}O)_x-OR$ wherein n has an average value from 1 to 4, x has an average value from 2 to about 150, and R may be hydrogen or alkyl of 1 to about 12 carbon atoms. Illustrative of such polyalkylene ether groups are poly(oxyethylene), poly(oxypropylene), poly(oxyethyleneoxypropylene), poly(oxyethyleneoxybutylene), and the like. Y in formulas II and III above may be any anion which does not adversely affect the production of polyhydric alcohols in the practice of the present invention such as hydroxide; a halide, for instance fluoride, chloride, bromide and iodide; a carboxylate group, such as formate, acetate, propionate, and benzoate and the like; an alkoxide group such as methoxide, ethoxide, phenoxide, and the like; a functionally substituted alkoxide or phenoxide group such as methoxyethoxide, ethoxyethoxide, phenoxyethoxide and the like; a pyridinolate or quinolate group; and others. Preferably Y in formulas II and III, above, is a carboxylate, most preferably formate, acetate and benzoate.

A suitable method for preparing the bis(triorgano phosphine)iminium salts is disclosed in an article by Appel, R. and Hanas, A. appearing in Z. Anorg. u. Allg. Chem., 311, 290, (1961).

Other organic salts useful in the practice of the present invention include the quaternized heterocyclic amine salts such as the pyridinium, piperidinium, morpholinium, quinolinium salts and the like. e.g., N-ethylpyridinium fluoride, N-methylmorpholinium benzoate, N-phenylpiperidinium hydroxide, N,N'-dimethyl-2,2-bipyridinium acetate, and the like.

In one of the embodiments of the present invention, the anion of the above salt promoters may be any of the rhodium carbonyl anions. Suitable rhodium carbonyl anions include $[Rh_6(CO)_{15}]^{2-}$; $[Rh_6(CO)_{15}Y]^-$ wherein Y may be halogen, such as chlorine, bromine, or iodine, $[Rh_6(CO)_{15}(COOR'')]^-$ wherein R'' is lower alkyl or aryl such as methyl, ethyl, or phenyl; $[Rh_6(CO)_{14}]^{2-}$; $[Rh_7(CO)_{16}]^{3-}$; and $[Rh_{12}(CO)_{30}]^{2-}$.

Under reaction conditions where a salt promoter is employed the salt is desirably added with the initial charge of reactants in amounts of from about 0.5 to about 2.0 moles, preferably from about 0.8 to about 1.6 moles, and most preferably from about 0.9 to 1.4 moles of salt for every five atoms of rhodium present in the reaction mixture.

The Lewis base nitrogen promoters may be any of the Lewis base nitrogen or organic aza-oxa Lewis base compounds defined above. Preferably the Lewis base nitrogen promoters are amines. This also includes those compounds where the nitrogen is part of a heterocyclic ring such as the pyridines, pyrimidines, piperidines, morpholines, quinolines and the like. Illustrative of these preferred Lewis base promoters are pyridine, 2,4,6-trimethylpyridine, 4-dimethylaminopyridine, 4-tridecylpyridine, isobutylamine, triethylamine, N-methylpiperidine, N-methylmorpholine, bis-(1,8)-dimethylaminonaphthalene, 1,4-diazabicyclo[2.2.2]-octane, and quinuclidine.

Under reaction conditions where a Lewis base nitrogen compound is used as a promoter it is preferably used in amounts from about 0.02 to about 2 equivalents of promoter, most preferably from about 0.1 to about 1 equivalent of promoter, for every mole of rhodium in the reaction mixture. The number of equivalents of promoter is equal to the number of moles of promoter times the number of nitrogen atoms in each molecule.

Mixtures of the above salt and amine low pressure promoters may be used in the practice of the present invention.

The salt and/or Lewis base nitrogen low pressure promoters may be added to the reaction in compound form or there may be added to the reactor any substance capable of generating the salt and/or the amine promoter in situ either prior to or during the reaction conditions of the present invention.

For instance an amide such as formamide, urea, and the like or an oxime may be added to the reactor in place of the amine promoter.

Another and preferred group of low pressure promoters include the trialkanolamine borates, preferably those having the formula:

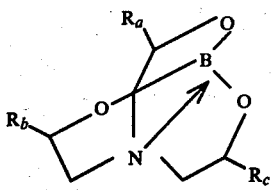

wherein $R_a$, $R_b$, and $R_c$ may be at least one of hydrogen or lower alkyl having from 1 to 12 carbon atoms in the alkyl chain. Most preferably the trialkanolamine borates useful in the practice of the present invention are triethanolamine borate and triisopropanolamine borate.

The quantity of catalyst employed is not narrowly critical and can vary over a wide range. In general, the novel process is desirably conducted in the presence of a catalytically effective quantity of the active rhodium species which gives a suitable and reasonable reaction rate. Reaction proceeds when employing as little as about $1 \times 10^{-6}$ weight percent, and even lesser amounts, of rhodium metal based on the total weight of reaction mixture. The upper concentration limit can be quite high, e.g., about thirty weight percent rhodium, and higher, and the realistic upper limit in practicing the invention appears to be dictated and controlled more by economics in view of the exceedingly high cost of rhodium metal and rhodium compounds. Depending on various factors such as the promoter of choice, the partial pressures of hydrogen and oxides of carbon, the total operative pressure of the system, the operative temperature, the choice of the organic co-diluent, and other considerations, a catalyst concentration of from about $1 \times 10^{-5}$ to about 5 weight percent rhodium (contained in the complex catalyst) based on the total weight of reaction mixture, is generally desirable in the practice of the invention.

The operative temperature which may be employed can vary over a wide range of elevated temperatures. In general, the novel process can be conducted at a temperature between about 100° C. and upwards approximately 375° C., and higher, sufficient to produce the desired alkane polyol. Operative temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, signs of some catalyst instability are noted. Notwithstanding this factor, reaction continues and polyhydric alcohols and/or their derivatives are produced. Additionally, one should take notice of the equilibrium reaction for forming ethylene glycol:

$$2CO + 3H_2 \rightleftharpoons HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Suitable operative temperatures are between about 150° C. to about 320° C., and desirably from about 210° C. to about 300° C.

The novel process is effected for a period of time sufficient to produce the desired polyfunctional oxygen-containing products and/or derivatives thereof. In general, the residence time can vary from minutes to several hours, e.g., from a few minutes to approximately 24 hours, and longer. It is readily appreciated that the residence period will be influenced to a significant extent by the reaction temperature, the concentration and choice of the catalyst, the total gas pressure and the partial pressure exerted by its components, the concentration, and other factors. The synthesis of the desired product(s) by the reaction of hydrogen with an oxide of carbon is suitably conducted under operative conditions which give reasonable reaction rates.

The relative amounts of oxide of carbon and hydrogen which are initially present in the reaction mixture can be varied over a wide range. In general, the mole ratio of $CO:H_2$ is in the range of from about 20:1 to about 1:20, suitably from about 10:1 to about 1:10, and preferably from about 5:1 to about 1:5.

It is to be understood, however, that molar ratios outside the aforesaid broad range may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, polyhydric alcohols are obtained by using mixtures containing carbon dioxide and hydrogen. Mixtures of carbon dioxide, carbon monoxide and hydrogen can also be employed. If desired, the reaction mixture can comprise steam and carbon monoxide.

The novel process can be executed in a batch, semicontinuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperatures due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the novel process especially to maintain the desired molar ratios of and the partial pressures exerted by the reactants.

As intimated previously, the operative conditions can be adjusted to optimize the conversion of the desired product and/or the economics of the novel process. In a continuous process, for instance, when it is preferred to operate at relatively low conversions, it is generally desirable to recirculate unreacted synthesis gas with-/without make-up carbon monoxide and hydrogen to the reaction. Recovery of the desired product can be achieved by methods well-known in the art such as by distillation, fractionation, extraction, and the like. A fraction comprising rhodium catalyst, generally contained in byproducts and/or solvents, can be recycled to the reaction zone, if desired. All or a portion of such fraction can be removed for recovery of the rhodium values or regeneration to the active catalyst and can be intermittently added to the recycle stream or directly to the reaction zone.

The active forms of the rhodium carbonyl clusters may be prepared by various techniques. They can be preformed and then introduced into the reaction zone. Alternatively, any of the host of rhodium-containing substances as well as any of the low pressures promoters can be introduced into the reaction zone and, under the operative conditions of the process (which of course includes hydrogen and carbon monoxide), the active rhodium carbonyl cluster can be generated in situ. Illustrative of rhodium-containing substances which can be conveniently introduced or placed in the synthesis zone include, for example, rhodium oxide ($Rh_2O_3$), tetrarhodium dodecacarbonyl, dirhodium octacarbonyl, hexarhodium hexadecacarbonyl ($Rh_6(CO)_{16}$), rhodium(II) formate, rhodium(II) acetate, rhodium (II) propionate, rhodium(II) butyrate, rhodium(II) valerate, rhodium(III) naphthenate, rhodium dicarbonyl acetylacetonate, rhodium tri(acetylacetonate), rhodium trihydroxide, indenyl-rhodium dicarbonyl, rhodium dicarbonyl (1-phenylbutane-1,3-dione), tris(hexane-2,4-dionato)rhodium(III), tris(heptane-2,4-dionato)rhodium(III), tris(1-phenylbutane-1,3-dionato)rhodium(III), tris(3-methylpentane-2,4-dionato)rhodium(III), tris(1-cyclohexylbutane-1,3-dionato)rhodium(III), triacontacarbonyl rhodium salts and rhodium-containing compounds deposited on porous supports or carriers capable of providing rhodium carbonyls in solution, and others.

The preparation of the rhodium carbonyl complex compounds can be conveniently carried out in the solvent mixture. Tetrarhodium dodecacarbonyl, though of limited solubility, can be added to the solvent in a finely divided form. Any of several of the rhodium-containing compounds illustrated previously can be employed in lieu of tetrarhodium dodecacarbonyl. The organic Lewis bases such as pyridine, or other promoters, such as the aforedefined salt promoters, can also be added thereto. The rhodium carbonyl complex or cluster forming reaction can be effected under a carbon monoxide pressure, with or without $H_2$, of about 1 to 15 atmospheres, and higher, using a temperature of about 30° C. to about 100° C., for a period of time ranging from minutes to a few days, generally from about 30 minutes to about 24 hours. The resulting rhodium carbonyl complex contained in the solvent mixture is catalytically active in this process. In preparing the aforesaid complexes, one can suitably employ from about 0.01 to about 25 moles salt or Lewis base nitrogen promoters per mole of rhodium (contained in the rhodium compound used as a rhodium source). Ratios outside this stated range can be employed especially when it is desirable to use diluent quantities of the low pressure promoters.

The equipment arrangement and procedure which provides the capability for determining the existence of anionic rhodium carbonyl complexes or clusters having defined infrared spectrum characteristics, during the course of the manufacture of polyhydric alcohols from carbon monoxide and hydrogen, pursuant to this invention is disclosed and schematically depicted in U.S. Pat. No. 3,957,857, issued May 18, 1976, the disclosure of which is incorporated herein by reference.

A particularly desirable infrared cell constructure is described in copending U.S. Pat. No. 3,886,364, issued May 27, 1975 and its disclosure of a preferred cell construction is incorporated herein by reference.

The "oxide of carbon" as covered by the claims and as used herein is intended to mean carbon monoxide and mixtures of carbon dioxide and carbon monoxide, either introduced as such or formed in the reaction. Preferably the oxide of carbon is carbon monoxide.

The reaction of the present invention is conducted in what is believed to be a homogeneous liquid phase, which means that the catalyst, the reaction products and the promoter if present are in solution. Though the reaction to produce alcohols is essentially homogeneous, there may be small amounts of insoluble catalyst particles depending on the reaction conditions employed.

The following examples are merely illustrative and are not presented as a definition of the limits of the invention.

The sulfolane used in the following examples was purified prior to use according to the method disclosed by E. N. Arnett and C. F. Douty, reported in the Journal of the American Chemical Society, 86, 409 (1964).

Other materials used in the following examples possessed the following characteristics: cesium benzoate—"$PhCO_2Cs$" (recrystallized from $H_2O$, Analysis—Found: C, 32.62; H, 1.90. Calcd. for $C_7H_5O_2Cs$: C, 33.10, H, 1.98); p-$MeSO_2C_6H_4CO_2Cs$, cesium para-methylsulfonylbenzoate (recrystallized from $H_2O$, Analysis—Found: C, 28.26; H, 2.05. Calcd. for $C_8H_7O_4SCs$: C, 28.90; H, 2.13). [18]-crown-6, [15]-crown-5 and dicyclohexyl-[18]-crown-6 solvent were obtained from Parish Chemical Company, Provo, Utah. The [18]-crown-6 was heated under vacuum to remove possible volatile impurities and its purity was checked by vpc, nmr and melting point. The dicyclohexyl-[18]-crown-6 was used as obtaimed. The [15]-crown-5 was distilled from sodium methoxide followed by a careful distillation on a spinning band column. It was 99.5=% pure, as determined by gas chromatography and contained between 16 to 28 ppm Cl.

In the examples below as set forth in the tables below, the following procedure was employed:

A 150 ml. capacity stainless steel reactor capable of withstanding pressures up to 7,000 atmospheres was charged with a premix of 75 cubic centimeters (cc) of a specified solvent, a specified amount of rhodium in the form of rhodium dicarbonylacetylacetonate, and specified amounts of one or more of an amine promoter (where indicated) and salt promoter (where indicated). The reactor was sealed and charged with a gaseous mixture containing equal molar amounts of carbon monoxide and hydrogen to a pressure as specified below. Heat was applied to the reactor and its contents; when the temperature of the mixture inside the reactor reached 190° C., as measured by a suitably placed thermocouple, an additional adjustment of carbon monoxide and hydrogen ($H_2:CO=1:1$ mole ratio) was made to bring the pressure back to that which is specified in the tables. The temperatures and pressures were maintained as indicated in the tables.

After the reaction was terminated, the vessel and its contents were cooled to room temperature, the excess gas vented and the reaction product mixture was removed. Analysis of the reaction product mixture was made by gas chromatographic analysis using a Hewlett Packard FM ™ model 810 Research Chromatograph.

Analysis of the product mixture in terms of ethylene glycol (hereinafter referred to in tables as "glycol") and methanol, are shown in the tables, as well as the rhodium recovery based on the total rhodium charged to the reactor.

Rhodium recovery was determined by atomic absorption analysis of the contents of the reactor after the venting of the unreacted gases at the end of the reaction. The rhodium recovery values may be characterized as the percent rhodium based on the total rhodium charged to the reactor that is soluble or suspended in the reaction mixture after the specified reaction time.

TABLE I

| Promoter(s)[b] | [18]-crown - 6 Solvent[a] | | Rate[c], M hr$^{-1}$, to | | Rh Recovered from Sample |
| --- | --- | --- | --- | --- | --- |
| | Rh(CO)$_2$acac, mmoles | Temp. | MeOH | Glycol | |
| | at 8,000 psi | | | | |
| 0.75 KOAc | 3 | 240° | 0.94 | 0.82 | 76 |
| | at 12,500 psi | | | | |
| 0.75 KOAc | 3 | 260 | 1.0 | 1.0 | 14 |
| 0.65 PhCO$_2$Cs + 1.25 pyridine | 3 | 247 | 1.9 | 2.5 | 82 |
| 0.75 PhCO$_2$Cs | 3 | 260 | 3.8 | 3.6 | 77 |
| 0.65 PhCO$_2$Cs | 3 | 260 | 5.4 | 5.6 | 65 |
| 0.65 PhCO$_2$Cs + 1.25 pyridine | 3 | 260 | 4.3 | 6.3 | 75 |
| 0.65 PhCO$_2$Cs + 2.5 pyridine | 3 | 260 | 4.0 | 5.8 | 86 |
| — | 3 | 270 | 1.0 | 0.12 | 5 |
| 0.65 PhCO$_2$Cs + 2.5 pyridine | 3 | 270 | 4.5 | 5.4 | 76 |
| 0.75 PhCO$_2$Cs + 10.0 N-methylmorpholine | 3 | 250[d] | 3.3 | 5.2 | 95 |
| 0.75 PhCO$_2$Cs + 10.0 N-methylmorpholine | 3 | 260 | 4.5 | 7.0 | 96 |
| 0.75 PhCO$_2$Cs + 10.0 N-methylmorpholine | 3 | 270 | 7.4 | 8.6 | 91 |
| 0.375 PhCO$_2$Cs + 4.0 N-methylmorpholine | 1.5 | 270[e] | 9.9 | 8.7 | 92 |
| 0.375 PhCO$_2$Cs + 7.0 N-methylmorpholine | 1.5 | 270 | 6.1 | 6.7 | 96 |

[a] 1/1 H$_2$/CO, 75 ml solvent
[b] Amounts are mmoles
[c] Scaled proportionately to 6 mmoles of Rh(CO)$_2$acac.
[d] During reaction about a 20 min. deviation in the temperature to about 258° C. was noted afterwhich the temperature was brought under control.
[e] Same as d. above but the deviation was to 275° C.

TABLE II.

| Promoter(s)[b] | [18]-crown-6/Sulfolane Solvent[a] (C) (S) | | | Rate[c], M hr$^{-1}$, to | | % Rh Recovered from Sample |
| --- | --- | --- | --- | --- | --- | --- |
| | Rh(CO)$_2$acac, mmoles | C/S(V/V) | Temp. | MeOH | Glycol | |
| 0.325 PhCO$_2$Cs + 1.25 pyridine | 1.5 | 24/76 | 270 | 5.5 | 5.1 | 94 |
| 0.325 PhCO$_2$Cs + 1.25 pyridine | 1.5 | 50/50 | 270 | 6.9 | 6.7 | 108 |
| 0.375 PhCO$_2$Cs + 2.5 pyridine | 1.5 | 50/50 | 275 | 9.7 | 7.7 | 88 |
| 0.325 PhCO$_2$Cs + 1.25 pyridine | 1.5 | 50/50 | 280 | 2.0 | 1.7 | 60 |
| 0.75 PhCO$_2$Cs + 7.0 ethylenedimorpholine | 3.0 | 50/50 | 275 | 7.6 | 7.5 | 93 |
| 0.375 PhCO$_2$Cs + 4.0 ethylenedimorpholine | 1.5 | 50/50 | 275 | 11. | 11. | 83 |
| 0.375 PhCO$_2$Cs + 4.0 ethylenedimorpholine | 1.5 | 50/50 | 275 | 10. | 11. | 92 |
| 0.375 PhCO$_2$Cs + 7.0 ethylenedimorpholine | 1.5 | 50/50 | 275-9[d] | 9.8 | 8.7 | 82 |
| 0.375 PhCO$_2$Cs + 4.0 ethylenedimorpholine | 1.5 | 24/76 | 275 | 6.8 | 6.8 | 84 |

[a] 1/1 H$_2$/CO, 75 ml solvent, 12,500 psi.
[b] Amounts are mmoles.
[c] Scaled proportionately in 6 mmoles of Rh(CO)$_2$acac.
[d] ~ 12200 psi.

TABLE III

| [18]-crown-6/Tetraglyme Solvent[a] | | | |
| --- | --- | --- | --- |
| [18]-crown-6[b] /Tetraglyme content (ratio) v/v | Rate[c], M hr$^{-1}$, to | | % Rh Recovered from Sample. |
| | MeOH | Glycol | |
| 100/0 | 8.0 | 14 | 96 |
| 76/24 | 4.8 | 10 | 90 |
| 50/50 | 3.4 | 10 | 85 |
| 40/60 | 3.7 | 8.9 | 76 |

[a] 1/1 H$_2$/CO, 75 ml solvent, 1.5 mmoles Rh(CO)$_2$acac, 0.375 mmole cesium benzoate, 4 mmoles-N-methylmorpholine 15,000 psi, 270° C.
[b] Contained less than 30 ppm Cl
[c] Scaled proportionately to 6 mmoles of Rh (CO)$_2$acac.

TABLE IV.

| Promoter(s)[b] | [18]-crown-6-Solvent-Tetrahydrofuran(THF)[a] | | Rate[c], M hr$^{-1}$ to | |
| --- | --- | --- | --- | --- |
| | Rh(CO)$_2$acac mmoles | C/THF(V/V) | MeOH | Glycol |
| 0.325 PhCOOCs + 1.25 pyridine | 1.5 | 50/50 | 1.04 | .72 |

TABLE IV.-continued

| | [18]-crown-6-Solvent-Tetrahydrofuran(THF)[a] | | | |
|---|---|---|---|---|
| | Rh(CO)$_2$acac | | Rate[c], M hr$^{-1}$ to | |
| Promoter(s)[b] | mmoles | C/THF(V/V) | MeOH | Glycol |
| 0.325 PhCOOCs + 1.25 pyridine | 1.5 | 0/100[d] | 0.76 | .18 |

[a]1/1 H$_2$/CO, 75 ml solvent, 12,500 psi, 270,C.
[b]Amounts are mmoles
[c]Scaled proportionally to 6 mmoles of Rh(CO)$_2$acac
[d]Pressure was 13,000 psi

TABLE V.

Pre-heating to compare stability of [18]-crown-6 and Tetraglyme

| Pre-heating Conditions | Reaction Conditions[a] | Rate, M hr$^{-1}$, to MeOH | Glycol | % Rh Recovered from Sample |
|---|---|---|---|---|
| | tetraglyme | | | |
| — | 0.75 PhCO$_2$Cs | 1.6 | 1.6 | 48 |
| 280°, 5 hr[b] | 0.75 PhCO$_2$Cs [18]Crown-6 | 1.13 | 0.77 | 36 |
| — | 0.65 PhCO$_2$Cs | 2.2 | 3.2 | 75 |
| 280°, 5 hr[c] | 0.65 PhCO$_2$Cs | 2.4 | 3.2 | 63 |

[a]1/1 H$_2$/CO, 75 ml solvent, 260°, 12,500 psi, 3 mmoles Rh(CO)$_2$acac, 1.25 pyridine. Amounts are mmoles.
[b]After pre-heating, but before reaction, the solution was yellow. Its vapor phase chromatogram and NMR spectrum showed no extraneous peaks.
[c]After pre-heating, but before reaction, the solution had an extremely faint yellow tint. Its vapor phase chromatogram and NMR spectrum showed no extraneous peaks.

TABLE VI

Comparison Between [18]-crown-6 And Dicyclohexyl-[18]-crown-6 Solvents[a]*

| Solvent | Rate[b], M hr.$^{-1}$ Methanol | Glycol | % Rh Recovery |
|---|---|---|---|
| [18]-crown-6 | 4.5 | 9.7 | 89 |
| Dicyclohexyl-[18]-crown-6 | >0.5[c] | 5.1 | 66 |

[a]15,000 psi, 260° C., 1.5 mmoles Rh(CO)$_2$ acac, 0.375 mmoles cesium benzoate, 4 mmoles N,N'-ethylene-dimorpholine, 75 ml of the solvent, 1/1 H$_2$/CO.
[b]Scaled proportionately to 6 mmoles Rh(CO)$_2$ acac.
[c]Reaction mixture was removed from reactor to 90° C. Much of the methanol could have been lost at that time.
*This table illustrates the principle previously stated that the advantages of crown ethers decrease as the number of carbons in the crown ether increases in relation to a fixed number of ether oxygen.

TABLE VII

Use of [15]-crown-5 as Solvent[a]

| Promoters[c] | Rate[b], M hr$^{-1}$ Methanol | Glycol | % Rh Recovery |
|---|---|---|---|
| 0.375 Cesium benzoate, 4.0 N-methylmorpholine | 10 | 14 | 95 |
| 0.375 Potassium acetate, 4.0 N-methylmorpholine | 7.5 | 13 | 89 |
| 0.375 Sodium acetate, 4.0 N-methylmorpholine | 1.7 | 0.20 | 98 |
| 0.5 Cesium benzoate | 7.8 | 8.4 | 96 |
| 0.5 Potassium benzoate | 7.2 | 8.5 | 89 |

[a]15,000 psi, 270° C., 1.5 Rh(CO)$_2$ acac, 75 ml. [15]-crown-5, 1/1 H$_2$CO.
[b]Scaled proportionately to 6 mmoles Rh(CO)$_2$ acac.
[c]In millimoles

What is claimed is:

1. In the process which comprises making alkane polyols by reacting hydrogen and oxides of carbon in a solvent solution containing a rhodium carbonyl complex the improvement which comprises employing as a solvent a crown ether consisting essentially of carbon, hydrogen and oxygen.

2. The process of claim 1 wherein the solvent is employed with a co-solvent.

3. The process of claim 2 wherein the co-solvent is tetraglyme, or sulfolane or butyrolactone.

4. The process of claim 1 wherein the crown ether contains not more than 100 ether oxygen atoms in the principal ring thereof.

5. The process of claim 4 wherein the crown ether contains 4 to 15 ether oxygens in the principal ring thereof.

6. The process of claim 5 wherein the crown ether is [18]-crown-6.

7. The process of claim 5 wherein the cr crown ether is [15]-crown-5.

8. The process of claim 3 wherein the crown ether is [18]-crown-6.

9. The process of claim 3 wherein the crown ether is [15]-crown-5.

* * * * *

UNITED STATES PATENT AND TRADEMARK OFFICE
CERTIFICATE OF CORRECTION

PATENT NO. : 4,162,261
DATED : July 24, 1979
INVENTOR(S) : Leonard Kaplan

It is certified that error appears in the above-identified patent and that said Letters Patent are hereby corrected as shown below:

Column 8, line 29, for "much" read -- such --. Column 9, lines 36-38, that portion of the formula reading $$°R°°°$$ should read $$·R°°°$$

Column 15, lines 28-31, that portion of the formula reading $$P - N - P$$ should read $$P = N = P$$

Column 15, line 48, for "for" read -- or --. Columns 21-22, Table II, in footnote c, for "in" read -- to --. Column 24, line 45, before "crown" delete "cr".

Signed and Sealed this

*First* Day of *July 1980*

[SEAL]

*Attest:*

SIDNEY A. DIAMOND

*Attesting Officer*        *Commissioner of Patents and Trademarks*